United States Patent [19]
Cheng et al.

[11] Patent Number: 6,040,905
[45] Date of Patent: Mar. 21, 2000

[54] FIBER COLOR GRADING SYSTEM

[75] Inventors: Luo Cheng; Glenn E. Irick, Sr.; Youe-Tsyr Chu; Hossein M. Ghorashi; Michael E. Galyon; Mark A. Overbay, all of Knoxville, Tenn.

[73] Assignee: Zellweger Uster, Inc., N.C.

[21] Appl. No.: 09/129,271

[22] Filed: Aug. 5, 1998

[51] Int. Cl.[7] .................................................. G01N 21/00
[52] U.S. Cl. ...................................... 356/238.3; 209/509
[58] Field of Search ................................ 356/238.3, 383, 356/385, 245; 73/160; 209/509, 511, 524–526, 536, 576, 577, 580, 587; 250/574, 559.01

[56] References Cited

U.S. PATENT DOCUMENTS 5,813,542   9/1998   Cohn ........................................ 356/406

OTHER PUBLICATIONS

Duckett, Cheng, Zapletalova, Watson, Ghorashi, *Additional Factors for HVI Color Grading*, 1198 Proceedings of the Beltwide Cotton Conference, Jan. 5, 1998.
Duckett, Cheng, *Color Grading*, Tenth Annual Engineered Fiber Selection System Conference, May 12–14, 1997.
B. Xu, C. Fang, and M.D. Watson, *Chromatic Image Analysis for Cotton Trash and Color Measurements*, Cotton Quality Measurements Conference, pp. 532–540, 1997.
Zellweger Uster, Uster HVI 900 brochure, date unknown.
Zellweger Uster, Uster LVI brochure, date unknown.

*Primary Examiner*—Frank G. Font
*Assistant Examiner*—Tu T. Nguyen
*Attorney, Agent, or Firm*—Luedeka, Neely & Graham, PC

[57] ABSTRACT

A fiber classing device having a sample window for viewing a fiber sample. A light source provides light that is directed toward and reflected by the fiber sample, producing reflected light. A photo sensitive detector is positioned to receive the reflected light, and it detects lightness, redness, and yellowness of the fiber sample. Processing means assign a preliminary grade to the fiber sample based at least in part on the lightness and yellowness of the fiber sample. The processing means also selectively adjust the preliminary grade to a final grade based at least in part on the redness of the fiber sample. The photo sensitive detector has one or more of a spectrometer, a camera, or a set of three photo diodes. A first photo diode detects light with a wavelength of between about 505 nanometers and about 605 nanometers, corresponding to the lightness of the fiber sample. A second photo diode detects light with a wavelength of between about 430 nanometers and about 530 nanometers, corresponding to the yellowness of the fiber sample. The third photo diode detects light with a wavelength of between about 550 nanometers and about 650 nanometers, corresponding to the redness of the fiber sample. The processing means analyzes the information from the photo sensitive detector to determine the mean redness, variance in lightness, variance in redness, variance in yellowness, contrast in lightness, percent of yellow spots, and contrast in yellowness of the fiber sample. The selective adjustment from the preliminary grade to the final grade is based at least in part on these parameters.

20 Claims, 3 Drawing Sheets

FIBER COLOR GRADING SYSTEM

FIELD OF THE INVENTION

The present invention is directed to fiber grading. More particularly the invention relates to detecting visual properties of fiber using photo sensitive instrumentation and using the detected visual properties to assign a grade to the fiber.

BACKGROUND OF THE INVENTION

One of the properties used to class fiber such as cotton is the color of the fiber. Traditionally, the classification of fiber relies predominantly upon the senses and judgement of human classers who visually inspect a fiber sample and assign it a grade accordingly.

There are incentives to replace human classers with high-volume instrumentation. For example, instrumentation generally tends to be faster, more reliable, more repeatable, and less expensive than the manual labor which it replaces. However, in side-by-side tests, prior-art classification instrumentation tends to assign a higher grade to the fiber samples tested than do human classers. Therefore, such instrumentation has not replaced human classers in final or more critical classification steps.

What is needed, therefore, is a system for detecting visual properties of fiber samples and assigning grades to the fiber samples, where the correlation between the grades assigned by the system have a better correlation to the grades assigned by human classers than do the present fiber classification devices.

SUMMARY OF THE INVENTION

The needs expressed above, and other needs, are met in the present invention by a fiber classing device having a sample window for viewing a fiber sample. A light source provides light that is directed toward and reflected by the fiber sample, producing reflected light. A photo sensitive detector is positioned to receive the reflected light and detect lightness, redness, and yellowness of the fiber sample. Processing means assign a preliminary grade to the fiber sample based at least in part on the lightness and yellowness of the fiber sample. The processing means also selectively adjust the preliminary grade to a final grade based at least in part on the redness of the fiber sample.

The redness of the fiber sample is a characteristic of the fiber sample that prior art instruments do not account for. Thus, by selectively adjusting the preliminary grade based at least in part on the redness of the fiber sample, a classing device according to the present invention produces grades that correlate better with the grades assigned by human classers. Therefore, a classing device according to the present invention can replace human classers.

In various preferred embodiments of the invention the photo sensitive detector includes one or more of a spectrometer, a camera, or a set of three photo diodes. A first photo diode detects light with a wavelength of between about 505 nanometers and about 605 nanometers, corresponding to the lightness of the fiber sample. A second photo diode detects light with a wavelength of between about 430 nanometers and about 530 nanometers, corresponding to the yellowness of the fiber sample. The third photo diode detects light with a wavelength of between about 550 nanometers and about 650 nanometers, corresponding to the redness of the fiber sample. As described herein, the three wavelength ranges of about 505 nanometers to about 605 nanometers, 430 nanometers to about 530 nanometers, and 550 nanometers to about 650 nanometers correspond generally to ranges of green light, blue light, and red light, respectively. However, the terms lightness, yellowness, and redness, respectively, are used herein as general designations for the three wavelength ranges, to indicate the general purpose for which each of the signals produced by the sensors detecting the wavelength ranges are used.

The processing means analyze the information from the photo sensitive detector to determine the mean redness, variance in lightness, variance in redness, variance in yellowness, contrast in lightness, percent yellow spots, and contrast in yellowness of the fiber sample. The selective adjustment from the preliminary grade to the final grade is based at least in part on at least one of these parameters.

In a method for classing a fiber sample according to the present invention, the fiber sample is viewed through a sample window. A light source is energized to produce light that is directed toward and reflected by the fiber sample, producing reflected light. A first intensity of the reflected light is detected within a first wavelength range, and a lightness value is produced based at least in part on the first intensity. A second intensity of the reflected light is detected within a second wavelength range, and a yellowness value is produced based at least in part on the second intensity. A third intensity of the reflected light is detected within a third wavelength range, and a redness value is produced based at least in part on the third intensity.

The lightness value and the yellowness value are analyzed to produce a composite value and a preliminary grade is assigned to the fiber sample based at least in part on the composite value. In a preferred embodiment, the redness value is analyzed to determine a mean and a variance of the redness value, the lightness value is analyzed to determine the variance and contrast of the lightness value, and the yellowness value is analyzed to determine the variance and contrast of the yellowness value, and the percentage of yellow spots. The preliminary grade is selectively adjusted to a final grade based at least in part on the mean of the redness value, the variance of the lightness value, the variance of the redness value, the variance of the yellowness value, the contrast of the lightness value, the contrast of the yellowness value, and the percentage of yellow spots of the fiber sample.

BRIEF DESCRIPTION OF THE DRAWINGS

Further advantages of the invention will become apparent by reference to the detailed description of preferred embodiments when considered in conjunction with the following drawings, which are not to scale, in which like reference numerals denote like elements throughout the several views, and wherein.

DETAILED DESCRIPTION OF THE INVENTION

Figure 1:
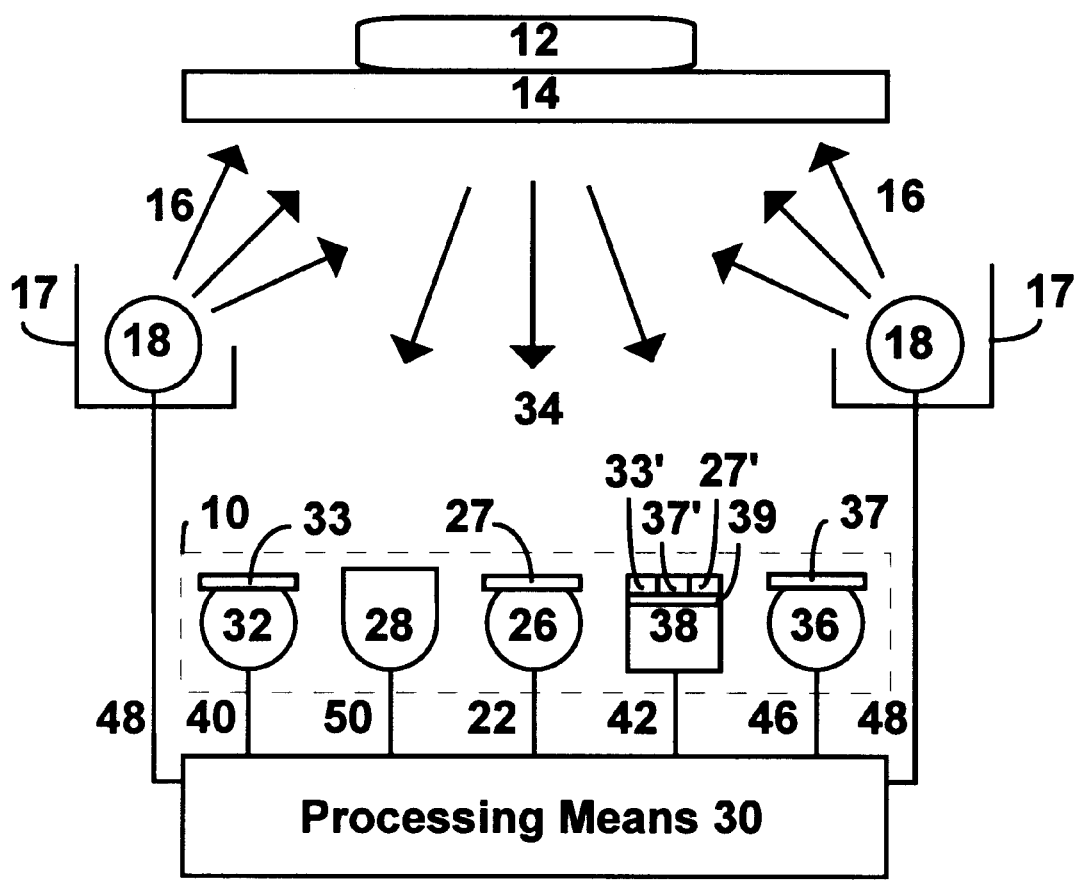
FIG. 1 is a functional block diagram of a fiber classing device.

Referring to FIG. 1, a classer 20 is illustrated that includes the present invention. The classer 20 is particularly useful for classing cotton. The classer 20 may be used in either an off-line mode where the classer 20 is a separate piece of equipment that may be located in a laboratory, or an on-line mode where the classer 20 is integrated with processing equipment that may be located in a gin or a mill. When used in an on-line mode, the classer 20 may be a part of a control system that controls the operation of the equipment to which it is attached.

To use the classer 20 to assign a grade to a fiber sample 12, the fiber sample 12 is placed in front of a sample window 14. The sample window 14 is preferably formed of a material that is relatively transparent to certain wavelengths of light as described more completely below. For example, the sample window 14 may be formed of glass, quartz, sapphire, or appropriate thermoplastic resins, and is preferably formed of water clear PYREX.

When the fiber sample 12 passes the sample window 14, the fiber sample 12 is illuminated, such as by energizing shielded bulbs 18 to produce light 16. The bulbs 18 are controlled by signals carried on lines 48 from a processing means 30. In various embodiments the bulbs 18 may be constantly illuminated or, alternately, may be pulsed at either a specific frequency or when there is a fiber sample 12 behind the sample window 14.

The fiber sample 12 reflects the light 16, thereby producing reflected light 34. The reflected light 34 is received by a photo sensitive detector 10. The light 16 from the bulbs 18 is shielded with shields 17 so that it does not directly illuminate the detector 10, which detects at least the lightness, designated as L*, the redness, designated as a*, and the yellowness, designated as b*, of the fiber sample 12 from the properties of the reflected light 34. This detection may be done in any one or more of a number of different ways, as described below.

In a first preferred embodiment the photo sensitive detector 10 is a set of three photo sensitive diodes. A photo sensitive diode 32 receives the reflected light 34 through a filter 33 and detects the intensity of the reflected light 34 in a first wavelength range, preferably of between about 505 nanometers and about 605 nanometers. A blue enhanced silicon diode model number SD290-12-22-241 manufactured by Advanced Photonix, Inc. of Camarillo Calif. is suitable for use as diode 32 and Cheshire County Optical of Jaffrey N.H. manufactures an appropriate filter 33. The photo sensitive diode 32 sends a voltage signal on line 40 to the processing means 30. The voltage signal on line 40 is proportional to the intensity of the reflected light 34 within the first wavelength range. The intensity of the reflected light 34 within the first wavelength range is designated as the lightness of the fiber sample 12. Therefore, the signal transmitted on line 40 is referred to as the lightness signal, which the processing means 30 converts to a lightness value.

A photo sensitive diode 36 receives the reflected light 34 through a filter 37 and detects the intensity of the reflected light 34 in a second wavelength range, preferably of between about 530 nanometers and about 430 nanometers. A blue enhanced silicon diode model number SD290-12-22-241 manufactured by Advanced Photonix, Inc. of Camarillo Calif. is suitable for use as diode 36 and Cheshire County Optical of Jaffrey N.H. manufactures an appropriate filter 37. The photo sensitive diode 36 sends a voltage signal on line 46 to the processing means 30. The voltage signal on line 46 is proportional to the intensity of the reflected light 34 within the second wavelength range. The intensity of the reflected light 34 within the second wavelength range is designated as the yellowness of the fiber sample 12. Therefore, the signal transmitted on line 46 is referred to as the yellowness signal, which the processing means 30 converts to a yellowness value.

A photo sensitive diode 26 receives the reflected light 34 through a filter 27 and detects the intensity of the reflected light 34 in a third wavelength range, preferably of between about 550 nanometers and about 650 nanometers. A blue enhanced silicon diode model number SD290-12-22-241 manufactured by Advanced Photonix, Inc. of Camarillo Calif. is suitable for use as diode 26 and Cheshire County Optical of Jaffrey N.H. manufactures an appropriate filter 27. The photo sensitive diode 26 sends a voltage signal on line 22 to the processing means 30. The voltage signal on line 22 is proportional to the intensity of the reflected light 34 within the third wavelength range. The intensity of the reflected light 34 within the third wavelength range is designated as the redness of the fiber sample 12. Therefore, the signal transmitted on line 22 is referred to as the redness signal, which the processing means 30 converts to a redness value.

Because the diodes 32, 36, and 26 are single-point detectors, each diode takes just one reading of the fiber sample 12 at a time. In other words, the diodes 32, 36, and 26 cannot detect or report changes in the intensity of the reflected light 34 across different portions of the fiber sample 12. Thus, the diodes 32, 36, and 26 provide bulk or mean measurements of the properties of the fiber sample 12.

In a second preferred embodiment the photo sensitive detector 10 is a camera 38, such as a charge coupled device (CCD). The camera 38 takes multiple, simultaneous readings on the fiber sample 12. By using a lens 39 to focus the reflected light 34 on the CCD array of the camera 38, each of the discrete sensors in the array primarily measures that portion of the reflected light 34 that originates from a specific portion of the fiber sample 12. Thus, distribution information in regard to the range of colors across the fiber sample 12 is preserved when using the camera 38. In other words, instead of taking a single averaged measurement of the fiber sample 12, as is done with each of the diodes 32, 36, and 26, the camera 38 takes a number of readings equal to the number of pixels in the array of the camera 38. This provides information about the range of colors within the fiber sample 12, where the averaged readings provided by the diodes 32, 36, and 26 do not.

Preferably, the camera 38 has an array size of about 512 pixels by about 480 pixels. The camera 38 detects the intensity of the reflected light 34 across a broader range of wavelengths than the first, second, and third range of wavelengths described above. Typically, the camera 38 will have elements to detect wavelengths correlating to red, green, and blue (RGB), which wavelengths have been standardized, such as by the National Television Systems Committee (NTSC). These RGB signals from the camera 38 are manipulated by processing means 30 to produce the lightness and yellowness values described above. These manipulations are described more fully hereafter. The output of the camera 38 is sent to the processing means 30 on a signal line 42, which produces the lightness, yellowness, and redness values described above.

While an eight bit camera 38 may be used, such as model MB-950C, manufactured by Polaris Industries of Atlanta Ga., a twelve bit camera 38 is preferred, so that the camera 38 has sufficient sensitivity to color gradations, enabling more accurate classing of the fiber sample 12. As twelve bit cameras are relatively expensive, the camera 38 may alternately be a set of three eight bit monochrome cameras, each fitted with a filter 33, 37 and 27 as described above for use with the diodes 32, 36, and 26. In this configuration, both sensitivity to color gradation and color distribution information are provided by the photo sensitive detector 10.

In a third preferred embodiment the photo sensitive detector 10 is a spectrometer 28, which detects the intensity of the reflected light 34 across essentially the entire range of the visible spectrum, and provides information about the intensity of the reflected light 34 at each wavelength, according to the specifications of the specific instrument used, rather than just within the three relatively broad wavelength ranges mentioned above. Model S-1000, manufactured by Ocean Optics of Dunedin, Fla. is a spectrometer that is suitable for this use. The output of the spectrometer 28 is sent to the processing means 30 on a signal line 50, which produces the lightness, yellowness, and redness values described above.

The three methods of detecting the reflected light 34 each provide relative benefits and drawbacks. The diodes 32, 36, and 26 are relatively inexpensive, but provide bulk measurements without distribution information. The spectrometer 28 accurately detects the intensity of the reflected light 34 at specific wavelengths, but is relatively expensive. The camera 38 provides distribution information, but unless the more expensive twelve bit camera is used, may not provide the sensitivity to color gradation required by all applications. Therefore, a decision as to which of the methods of detection to use is preferably based on factors such as the cost that the application can bear and the degree of accuracy required by the application.

In a most preferred embodiment, the photo sensitive detector 10 includes both a camera 38 and the set of three diodes 32, 36, and 26. In this manner, the camera 38 provides the distribution information and the diodes 32, 36, and 26 provide the color depth information within the first, second, and third wavelength ranges. In an alternate embodiment, all three of the various types of photo sensitive detectors described above are incorporated into the photo sensitive detector 10.

The measurements taken from the fiber sample 12 by the photo sensitive detector 10 are analyzed by the processing means 30. The processing means 30 may be a simple dedicated microprocessor or an entire computer. Preferably, the processing means 30 includes a power supply, an input/output for receiving and sending signals on the lines 22, 40, 42, 46, 48, and 50, an analog to digital converter, memory for storing data and processing instructions, and a microprocessor for processing data and instructions. Other items such as a user interface and a display may also be included in the processing means 30. The sophistication of the processing means 30 used to analyze the output of the photo sensitive detectors depends upon the complexity of the functions to be performed.

The voltage measurements received by the processing means 30 are not in the same form as cotton grades assigned by a human classer. Therefore, the processing means 30 of the classer 20 manipulates the signals produced by the photo sensitive detector 10 and produces a grade that is in the same form as that given by a human classer. This is preferably accomplished by correlating the lightness signal and the yellowness signal described above with the output signals produced by prior art high volume instrumentation. The output signals of the prior art instrumentation have already been correlated with the cotton grades assigned by human classers. However, the correlation between prior art instrumentation and human classers tends to be only about fifty percent. Therefore, the redness signal provided by a high volume instrument according to the present invention is additionally used to provide a higher degree of correlation.

Lightness of cotton is measured by prior art instrumentation in terms of a value known as Rd, referred to as reflectance. Normally, cotton has an Rd value of between about forty-eight and about eighty-two. The higher the Rd value, the lighter the cotton. The lightness signal produced by the photo sensitive detector 10 correlates generally to the Rd value produced by prior art instrumentation.

The yellowness of cotton is measured by prior art instrumentation in terms of a value known as +b, referred to as color. Normally, cotton has a +b value of between about five and about seventeen. The higher the +b value, the yellower the cotton. The yellowness signal produced by the photo sensitive detector 10 correlates generally similar to the +b value produced by prior art instrumentation.

The Rd and +b values are manipulated and combined to determine grades that are reported as two-digit numbers that vary in range from eleven to eighty-five. The first digit of the grade represents the lightness, or in other words the reflectance of the cotton, as determined from the Rd value. This first digit varies in value from one to eight. A one in the first position represents a lighter cotton sample while a seven designates a darker cotton sample. A value of eight represents subgrade cotton. The second digit of the grade represents the yellowness, or in other words the color of the cotton, as determined from the +b value. The second digit varies in value from one to five. A one in the second position represents a whiter cotton sample while a four designates a yellower cotton sample. A value of five represents subgrade cotton. A third digit may be used to further divide the class designated by the first two digits into subclasses according to the trash content and quality of the cotton.

Figure 2:
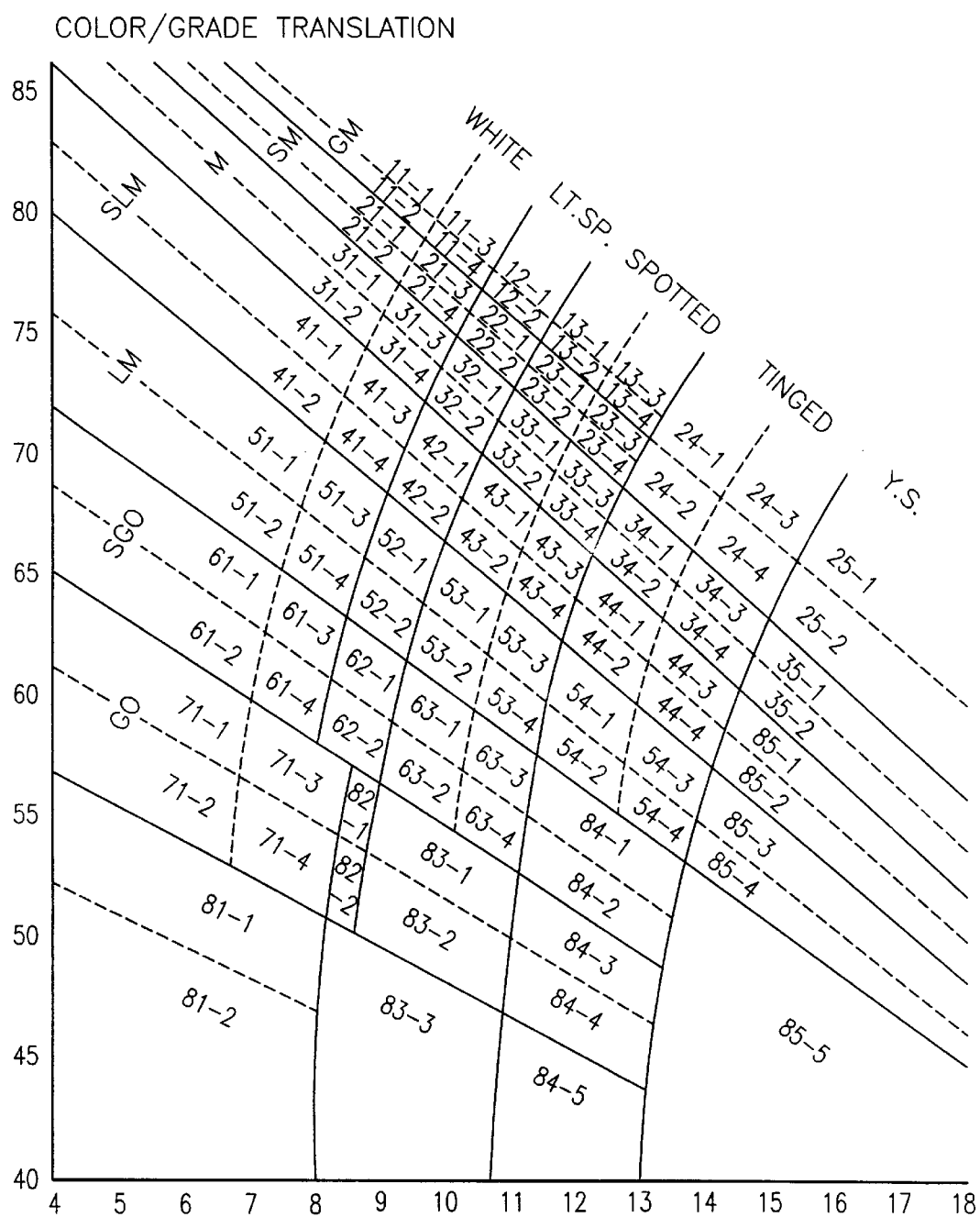
FIG. 2 depicts a cotton color chart.

The two-digit grades determined by the instrumentation are converted into the grades assigned by human classers by plotting the various grades on a official color chart regulated by the United States Department of Agriculture. In the United States, cotton color grades fall into one of five color groups: White, Light Spotted, Spotted, Tinged and Yellow Stained. This chart is represented in FIG. 2. Using historical data, the chart depicted in FIG. 2 has been empirically produced to correlate the grades assigned by instrumentation and the grades assigned by human classers.

For example, a particular cotton sample may produce readings that correspond to an Rd of seventy-four and a +b value of ten. By comparing these values to an internal version of the chart graphically depicted in FIG. 2, the prior art instrument designates a grade of thirty-two for the cotton fiber sample, and presents this value, such as on a display. The reflectance value of three represents a light grade of cotton referred to as Middling cotton. The color value of two further classifies the cotton sample as Light Spotted cotton. Thus, the cotton sample is classed as Light Spotted Middling cotton by the prior art instrument.

As previously mentioned, the historical correlation between the grade assigned by a prior art instrument and the grade assigned by a human classer is only about fifty percent. In other words, after a prior art instrument has determined the Rd value and the +b value, plotted these values on the chart of FIG. 2, and determined what the grade for the cotton sample should be from the overlying grade grid, the grade determined by the prior art instrument matches the grade assigned by a human classer only fifty percent of the time. It is a basic assumption in the field of art that the human classer is always correct.

The classer 20 of the present invention determines a preliminary grade in a manner similar to the prior art instruments by correlating lightness L* to reflectance Rd and yellowness b* to color +b. However, the classer 20 then uses other information to selectively adjust the preliminary grade to a final grade. This other information includes, inter alia, the mean of the redness signal, the variance of the lightness signal, the variance of the redness signal, the variance of the yellowness signal, the contrast of the lightness signal, and the contrast of the yellowness signal. The processing means 30 is used to determine all of these values from the signals provided by the photo sensitive detector 10.

The method by which the lightness L*, redness a*, and yellowness b* are computed by the processing means 30 differs depending upon the nature of the photo sensitive device 10. For example, the computations will differ depending upon whether the lightness, redness, and yellowness signals are being provided by the diodes 32, 36, and 26, the camera 38, or the spectrometer 28. The manner in which the lightness, redness, and yellowness values are produced are explained below for each of the representative types of photo sensitive devices 10 mentioned above.

When using the diodes 32, 36, and 26, the lightness, redness, and yellowness values are computed from equations that are dependent on the ranges selected for the first wavelength range, the second wavelength range, and the third wavelength range. To a certain extent, the exact ranges selected for the first, second, and third ranges are not critical, so long as they are known and the equations are adjusted accordingly. However, it is preferred to use ranges and equations that are well known.

Preferably, a color space defined by the Commission International de l'Eclairage (CIE), otherwise known as the International Commission of Illumination, is used. The first, second, and third wavelength ranges described above are selected to coincide with the color space defined by the CIE. A more complete description of the CIE color space is given in *Principles of Color Technology* by Billmeyer and Saltzman, John Wiley & Sons, 1981, the entire disclosure of which is incorporated herein by reference. However, it will be appreciated that other wavelength ranges and other color spaces could be selected.

Figure 3:
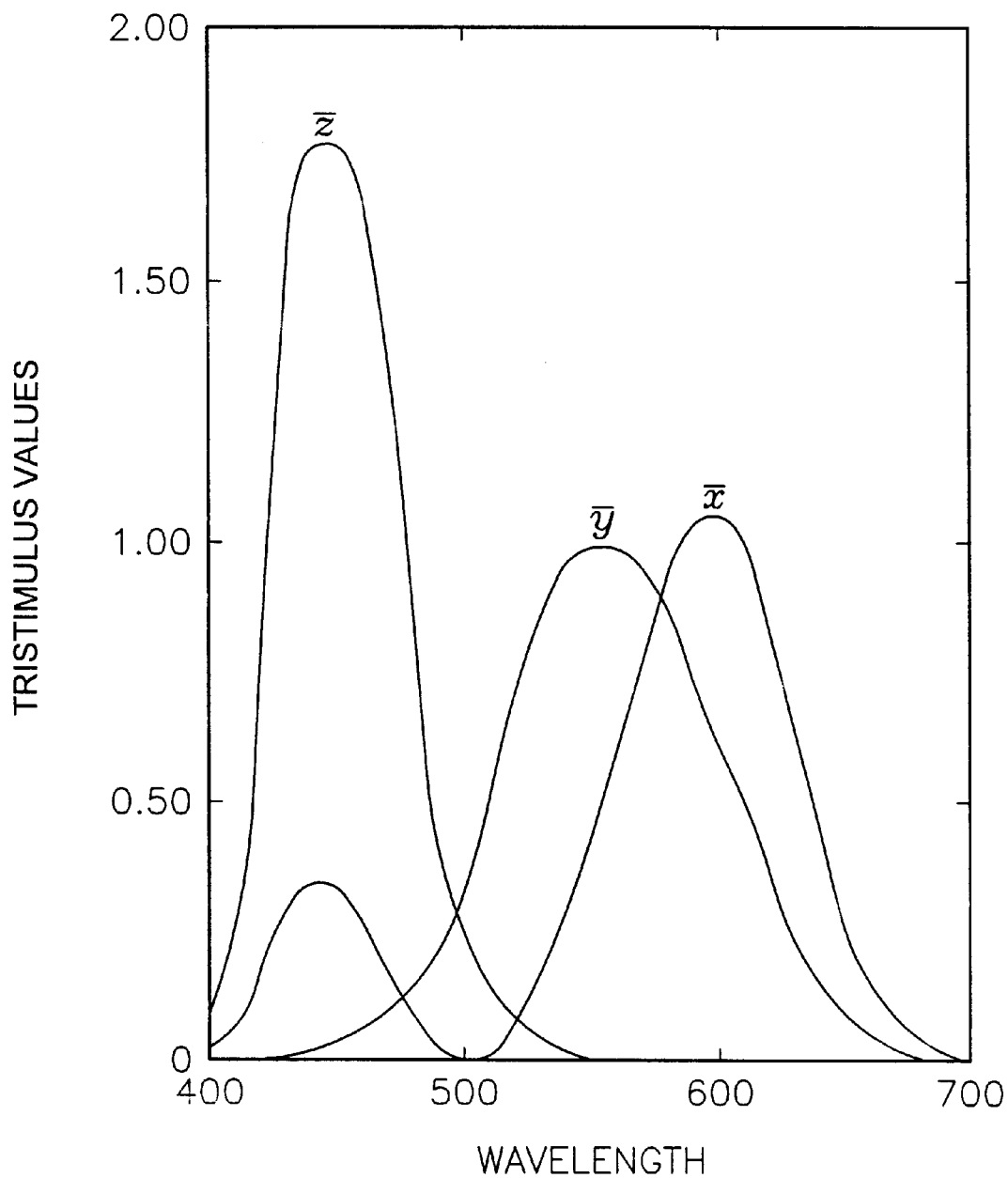
FIG. 3 depicts the 2° 1931 Standard Observer chart.

The intensities of the reflected light 34 within the first, second, and third wavelength ranges are measured by the diodes 32, 36, and 26, and correlate to the values charted in the 2° 1931 CIE Standard Observer, as depicted in FIG. 3. The lightness signal from the first diode 32 is used to calculate the tristimulus value Y, the redness signal from the third diode 26 and the yellowness signal from the second diode 36 are used to calculate the tristimulus value X, and the yellowness signal from the second diode 36 is used to calculate the tristimulus value Z. In each case, the voltage from the respective diode is calibrated to a known sample, and the voltage output of the diode thereafter is treated as a mean value for the fiber sample 12.

The redness signal is calculated by adding the voltage signals from the second and third diodes 36 and 26, where each voltage is multiplied by a constant prior to adding. These constants are determined empirically for each instrument during a calibration procedure where several graded fiber samples 12 are measured and the instrument is adjusted to agree with the grade assigned by a human classer.

The tristimulus values are used to calculate the lightness L*, redness a*, and yellowness b* values, using the equations given below:

$$L^* = 116\left(\frac{Y}{Y_n}\right)^{\frac{1}{3}} - 16$$

-continued $$b^* = 200\left[\left(\frac{Y}{Y_n}\right)^{\frac{1}{3}} - \left(\frac{Z}{Z_n}\right)^{\frac{1}{3}}\right]$$

$$a^* = 500\left[\left(\frac{X}{X_n}\right)^{\frac{1}{3}} - \left(\frac{Y}{Y_n}\right)^{\frac{1}{3}}\right]$$

Where $X_n$, $Y_n$, and $Z_n$ are the tristimulus values for ideal white, taken from standardized tables.

When using the spectrometer, the tristimulus values are determined by summing the intensity of the reflected light 34 across the detected range of wavelengths, most preferably from about four hundred nanometers to about seven hundred nanometers, according to the following equations:

$$X = \Sigma S(\lambda) R(\lambda) \bar{x}(\lambda)$$

$$Y = \Sigma S(\lambda) R(\lambda) \bar{y}(\lambda)$$

$$Z = \Sigma S(\lambda) R(\lambda) \bar{z}(\lambda)$$

Where $S(\lambda)$=relative spectral power, normally a CIE standard illuminant, $R(\lambda)$=reflectance intensity as measured at the indicated wavelength, $\lambda$=wavelength, and $\bar{x}(\lambda)$, $\bar{y}(\lambda)$, and $\bar{z}(\lambda)$ are read from the chart of FIG. 3.

The value for $S(\lambda)$ is detected by a sensor, such as a fourth diode, not depicted, but as described in application Ser. No. 08/962,973 filed Oct. 29, 1997, the entire disclosure of which is incorporated herein by reference, which diode detects the intensity of the light 16 produced by the bulbs 18 without detecting the intensity of the reflected light 34.

If three monochrome CCD cameras 38 are used, each fitted with one of the filters as described above, then the calculations described above for the diodes 32, 36, and 26 are performed on each set of three pixels taken from the same relative location within each of the three arrays.

When using the camera 38, the RGB values output are first converted to the X, Y, and Z tristimulus values, which are then converted to the L*, a*, and b* values using the equations given above. The RGB values are converted to the tristimulus values using the matrix equation below:

$$\begin{bmatrix} X \\ Y \\ Z \end{bmatrix} = \begin{bmatrix} 0.607 & 0.174 & 0.201 \\ 0.299 & 0.587 & 0.114 \\ 0.000 & 0.066 & 1.117 \end{bmatrix} \begin{bmatrix} R_{NTSC} \\ G_{NTSC} \\ B_{NTSC} \end{bmatrix}$$

Using the equations given above, the mean redness value a*, the mean lightness value L*, and the mean yellowness value b* can be calculated, regardless of the type of device used for the photo sensitive detector 10.

As mentioned above, lightness L* and yellowness b* correlate with reflectance Rd and color +b in a linear fashion. Thus, the lightness L* and the yellowness b* can be used to determine fiber grades using the cotton color chart, such as given in FIG. 2. However, the classer 20 also provides a great range of information not previously available from high volume instruments. The additional information extracted from the measured visual properties of the fiber sample 12 is used to improve the correlation between the grade assigned by the classer 20 and a human classer.

The additional information provided by the classer 20 is used to selectively determine a final grade, by training the processing means 30. One method of training the processing means 30 is to measure a given number of fiber samples 12, such as one hundred samples, and determine the preliminary grade for each fiber sample 12. The grades preliminarily assigned by the classer 20 are then compared to the grades assigned to the same fiber samples 12 by a human classer. The additional information provided by the classer 20 is then analyzed to determine final grades until a desired degree of correlation exists between the final grades assigned by the classer 20 and the grades assigned by the human classer.

It will be appreciated that there may be reasons for having a degree of correlation between the final grades of the classer 20 and the grades of the human classer that is less than the highest possible degree. For example, it may be desired to operate the classer 20 so that the final grades produced tend to err on the side of assigning a lower grade than the human classer would assign. In this example, there is a high degree of confidence that the final grades assigned by the classer 20 are not higher than the grades assigned by the human classer.

Alternately, it may be desired to operate the classer 20 so that final grades produced tend to err on the side of assigning a higher grade than the human classer would assign. In this example, there is a high degree of confidence that the final grades assigned by the classer 20 are not lower than the grades assigned by the human classer. Further, it may be desired to operate the classer 20 so that the final grades produced tend to match as closely as possible, on average, the grades assigned by the human classer. In this example, there is a high degree of confidence that the final grades assigned by the classer 20 are as close as possible to the actual grades assigned by the human classer, which actual grades may be higher or lower than the final grades assigned by the classer 20.

As a specific example, in tests conducted on the classer 20, using the mean redness value $a^*$ in selectively adjusting the preliminary grade (based on lightness and yellowness) to a final grade (based on lightness, yellowness, and redness) has improved the correlation between the grade assigned by an instrument and the grade assigned by a human classer from about fifty percent to about ninety-four percent. The mean redness value is preferably used to reduce the grade assigned by the classer 20 when the mean redness value is greater than a certain threshold limit. While this threshold limit may vary depending on the specific instruments used and fiber sample measured, a threshold limit of about 2.1 has provided a high degree of correlation when used to downgrade cotton from White to Light Spotted. Thus, in this embodiment, the mean redness value is preferably only used to adjust the preliminary grade to a final grade when two conditions exist: first, the cotton is preliminarily graded as White, and second, the mean redness value is greater than 2.1.

While the criteria described herein can be used to selectively adjust a preliminary grade to a final grade, regardless of what the preliminary grade is, in the preferred embodiment the selective adjustment is most meaningful on the higher, or whiter grades of fibers. For example, downgrading a preliminary grade of White to Light Spotted, or downgrading a preliminary grade of Light Spotted to Spotted.

As a further specific example, the variance in any or all of the lightness, redness, and yellowness can also be used to adjust the preliminary grade to the final grade. The variance is determined mathematically from the information provided by the camera 38, as it is capable of taking multiple simultaneous measurements on the fiber sample 12, as described above. Thus, distribution information in regard to the fiber sample 12 is used to calculate a mathematical variance.

The variance for each of the three values, lightness, redness, and yellowness, is calculated based on the differences between either individual pixel elements or blocks of pixels within the CCD array of the camera 38. In the preferred embodiment, the CCD array is divided into square blocks of multiple pixels, such as four pixels, nine pixels, sixteen pixels, etc., with all of the pixel blocks having the same size. The size of the pixel block is selected based on one or more of several different criteria, including the size of the CCD array, the size of the area of the fiber sample 12 to be imaged, the size of the anomalies within the fiber sample 12 to be detected, and the desired number of simultaneous data points. The mean value is calculated for each block and the variance is calculated using the mean value for each block.

In tests conducted on the classer 20, selectively downgrading the preliminary grade to a final grade when the variance in $b^*$ is greater than 1.1 has improved the correlation between grades assigned by the classer 20 and grades assigned by the human classer from about fifty percent to about seventy-six percent.

Another parameter within the information provided by the classer 20 that can be used to selectively adjust the preliminary grade to a final grade is the contrast in lightness, yellowness, or redness in the fiber sample 12. The contrast is determined by finding the highest and the lowest values for each of the three values as reported from the CCD array. The lowest value is then subtracted from the highest value to yield the contrast. Other mathematical techniques which indicate breadth of a range of values may also be used. In a most preferred embodiment, the contrast in redness $a^*$ is not used, as redness values are typically found to be within a very narrow range.

In tests conducted on the classer 20, selectively downgrading the preliminary grade to a final grade when the contrast in $b^*$ is greater than a threshold, determined as generally described herein, has improved the correlation between grades assigned by the classer 20 and grades assigned by the human classer from about fifty percent to about fifty-nine percent.

In a further embodiment, the total amount of area of the fiber sample 12 that exhibits a yellowness value $b^*$ greater than a threshold, determined as generally described herein, is used to selectively adjust the preliminary grade to a final grade. This is also called percent of yellow spots herein. In this embodiment, each yellowness value from the CCD array is compared to the threshold value. If the yellowness value is greater than the threshold, then a counter is incremented. The total number tabulated on the counter is then divided by the total number of elements within the CCD array. If this ratio is greater than a second threshold value, equal to about 0.05 in the tests conducted, then the preliminary grade of the fiber sample 12 is downgraded to a final grade.

The exact thresholds for the various parameters described above used by the processing means 30 to selectively determine a final grade will vary according several different factors. By way of example, these factors may include the characteristics of the light 16 produced by the bulbs 18, the material and thickness used for the sample window 14, the distance between the bulbs 18 and sample window 14, the distance between the sample window 14 and the photo sensitive detector 10, the type and sensitivity of the elements used within the photo sensitive detector 10 as discussed above, and the quality and consistency of the fiber samples 12.

Because of the number of factors which can affect the calibration of the processing means 30, fiber samples 12 having known grades assigned by human classers are preferably tested at regular intervals on the classer 20 to ensure that the calibration has not drifted. Further, as any one or more of these or other variables which influence the calibration of the processing means 30 changes, the processing means 30 is preferably retrained by correlating a number of samples with grades assigned by a human classer, as described above. In this manner, the various thresholds for the different parameters used to selectively adjust the preliminary grade to a final grade are adjusted until the classer 20 produces the same grades as those assigned by a human classer for a series of fiber samples.

Thus, a classer 20 according to the present invention provides information about the cotton sample 12 that is not provided by prior art high volume instrumentation. The classer 20 uses the additional information from the fiber sample 12 to selectively adjust the preliminary grade assigned to the fiber sample 12 to a final grade. The final grade assigned by the classer 20 has a higher degree of correlation to the grade assigned by human classers than does the grade assigned by prior art high volume instrumentation.

While specific embodiments of the invention have been described with particularity above, it will be appreciated that the invention comprehends rearrangement and substitution of parts within the spirit of the appended claims.

What is claimed is:

1. A fiber classing device comprising:
   a sample window for viewing a fiber sample,
   a light source for providing light that is directed toward and reflected by the fiber sample, producing reflected light,
   a photo sensitive detector positioned to receive the reflected light, for detecting lightness, redness, and yellowness of the fiber sample, and for producing a lightness signal, a redness signal, and a yellowness signal based on the lightness, redness, and yellowness of the fiber sample, and
   processing means for (1) receiving the lightness signal, redness signal, and yellowness signal from the photo sensitive detector, (2) assigning a preliminary grade to the fiber sample based at least in part on the lightness signal and yellowness signal, and (3) selectively adjusting the preliminary grade to a final grade based at least in part on the redness signal.

2. The device of claim 1 wherein the photo sensitive detector comprises:
   a first photo diode for detecting intensity of light within a first wavelength range corresponding to the lightness of the fiber sample.
   a second photo diode for detecting intensity of light within a second wavelength range corresponding to the yellowness of the fiber sample, and
   a third photo diode for detecting intensity of light within a third wavelength range corresponding to the redness of the fiber sample.

3. The device of claim 2 wherein the first wavelength range further comprises a wavelength range of between about 505 nanometers and about 605 nanometers.

4. The device of claim 2 wherein the second wavelength range further comprises a wavelength range of between about 430 nanometers and about 530 nanometers.

5. The device of claim 2 wherein the third wavelength range further comprises a wavelength range of between about 550 nanometers and about 650 nanometers.

6. The device of claim 1 wherein the photo sensitive detector comprises a spectrometer.

7. The device of claim 1 wherein the photo sensitive detector comprises a camera.

8. The device of claim 1 wherein the photo sensitive detector comprises:
   a first photo diode for detecting light within a wavelength range of between about 505 nanometers and about 605 nanometers, corresponding to the lightness of the fiber sample,
   a second photo diode for detecting light within a wavelength range of between about 430 nanometers and about 530 nanometers, corresponding to the yellowness of the fiber sample,
   a third photo diode for detecting light within a wavelength range of between about 550 nanometers and about 650 nanometers, corresponding to the redness of the fiber sample, and
   a camera.

9. The device of claim 1 wherein the photo sensitive detector comprises:
   a spectrometer, and
   a camera.

10. The device of claim 1 wherein the processing means selectively adjusts the preliminary grade to a final grade based at least in part on at least one parameter selected from the group consisting of mean redness, variance in lightness, variance in redness, variance in yellowness, contrast in lightness, percent yellowness, and contrast in yellowness of the fiber sample.

11. A fiber classing device comprising:
    a sample window for viewing a fiber sample,
    a light source for providing light that is directed toward and reflected by the fiber sample, producing reflected light,
    a photo sensitive detector positioned to receive the reflected light, for detecting the lightness, redness, and yellowness of the fiber sample, the photo sensitive detector having;
       a first photo diode for detecting light within a wavelength range of between about 505 nanometers and about 605 nanometers, corresponding to a mean lightness of the fiber sample,
       a second photo diode for detecting light within a wavelength range of between about 430 nanometers and about 530 nanometers, corresponding to a mean yellowness of the fiber sample,
       a third photo diode for detecting light within a wavelength range of between about 550 nanometers and about 650 nanometers, corresponding to a mean redness of the fiber sample, and
       a camera for detecting at least one parameter selected from the group consisting of variance in lightness, variance in redness, variance in yellowness, contrast in lightness, percent yellowness, and contrast in yellowness of the fiber sample, and
    processing means for assigning a preliminary grade to the fiber sample based at least in part on the mean lightness and mean yellowness of the fiber sample, and further for selectively adjusting the preliminary grade to a final grade based at least in part on the mean redness of the fiber sample.

12. The device of claim 11 wherein the processing means selectively adjusts the preliminary grade to a final grade additionally based at least in part on at least one of variance in lightness, variance in redness, variance in yellowness, contrast in lightness, percent yellowness, and contrast in yellowness of the fiber sample.

13. A method for determining fiber sample properties comprising:
  viewing a fiber sample through a sample window,
  energizing a light source to produce light that is directed toward and reflected by the fiber sample, thereby producing reflected light,
  detecting a first intensity of the reflected light within a first wavelength range,
  producing a lightness value based at least in part on the first intensity,
  detecting a second intensity of the reflected light within a second wavelength range,
  producing a yellowness value based at least in part on the second intensity,
  detecting a third intensity of the reflected light within a third wavelength range,
  producing a redness value based at least in part on the third intensity,
  analyzing the lightness value and the yellowness value to produce a composite value,
  assigning a preliminary grade to the fiber sample based at least in part on the composite value, and
  selectively adjusting the preliminary grade to a final grade based at least in part on the redness value of the fiber sample.

14. The method of claim 13 wherein the step of detecting a first intensity of the reflected light within a first wavelength range further comprises detecting a first intensity of the reflected light within a wavelength range of from about 505 nanometers to about 605 nanometers.

15. The method of claim 14 wherein the step of detecting a second intensity of the reflected light within a second wavelength range further comprises detecting a second intensity of the reflected light within a wavelength range of from about 430 nanometers to about 530 nanometers.

16. The method of claim 13 wherein the step of detecting a third intensity of the reflected light within a third wavelength range further comprises detecting a third intensity of the reflected light within a wavelength range of from about 550 nanometers to about 650 nanometers.

17. The method of claim 13 wherein the step of selectively adjusting the preliminary grade to a final grade based at least in part on the redness value of the fiber sample further comprises:
  analyzing the redness value to determine a mean of the redness value of the fiber sample, and
  selectively adjusting the preliminary grade to a final grade based at least in part on the mean of the redness value of the fiber sample.

18. The method of claim 13 wherein the step of selectively adjusting the preliminary grade to a final grade based at least in part on the redness value of the fiber sample further comprises:
  analyzing the lightness value to determine a variance of the lightness value of the fiber sample,
  analyzing the redness value to determine a variance of the redness value of the fiber sample,
  analyzing the yellowness value to determine a variance of the yellowness value of the fiber sample, and
  selectively adjusting the preliminary grade to a final grade based at least in part on the variance of the lightness value of the fiber sample, the variance of the redness value of the fiber sample, and the variance of the yellowness value of the fiber sample.

19. The method of claim 13 wherein the step of selectively adjusting the preliminary grade to a final grade based at least in part on the redness value of the fiber sample further comprises:
  analyzing the lightness value to determine a contrast of the lightness value of the fiber sample,
  analyzing the yellowness value to determine a contrast of the yellowness value of the fiber sample, and
  selectively adjusting the preliminary grade to a final grade based at least in part on the contrast of the lightness value of the fiber sample and the contrast of the yellowness value of the fiber sample.

20. The method of claim 13 wherein the step of selectively adjusting the preliminary grade to a final grade based at least in part on the redness value of the fiber sample further comprises:
  analyzing the redness value to determine a mean of the redness value of the fiber sample,
  analyzing the lightness value to determine a variance of the lightness value of the fiber sample,
  analyzing the redness value to determine a variance of the redness value of the fiber sample,
  analyzing the yellowness value to determine a variance of the yellowness value of the fiber sample,
  analyzing the lightness value to determine a contrast of the lightness value of the fiber sample,
  analyzing the yellowness value to determine a contrast of the yellowness value of the fiber sample,
  analyzing the yellowness value to determine a percentage of yellow spots of the fiber sample, and
  selectively adjusting the preliminary grade to a final grade based at least in part on the mean of the redness value, the variance of the lightness value, the variance of the redness value, the variance of the yellowness value, the contrast of the lightness value, the contrast of the yellowness value, and the percentage of yellow spots of the fiber sample.

* * * * *